US008899774B2

(12) United States Patent
Strong et al.

(10) Patent No.: US 8,899,774 B2
(45) Date of Patent: Dec. 2, 2014

(54) WEARABLE HEADLIGHT DEVICES AND RELATED METHODS

(75) Inventors: James Strong, Skaneateles, NY (US); Richard A. Tamburrino, Auburn, NY (US); John M. Ryan, Auburn, NY (US); Roger W. Leseberg, Syracuse, NY (US); Ervin Goldfain, Syracuse, NY (US); David M. Babson, Warners, NY (US); David Stephens, Skaneateles, NY (US); Angelo Martellaro, Bloomfield, NY (US)

(73) Assignee: Integra Lifesciences Corporation, Plainsboro, NJ (US)

( * ) Notice: Subject to any disclaimer, the term of this patent is extended or adjusted under 35 U.S.C. 154(b) by 68 days.

(21) Appl. No.: 13/069,288

(22) Filed: Mar. 22, 2011

(65) Prior Publication Data

US 2012/0120635 A1    May 17, 2012

Related U.S. Application Data

(60) Provisional application No. 61/414,739, filed on Nov. 17, 2010.

(51) Int. Cl.
*F21V 21/084* (2006.01)
*A61B 1/06* (2006.01)
*A61B 5/00* (2006.01)
*A42B 3/04* (2006.01)
*F21W 131/20* (2006.01)
*A61B 19/00* (2006.01)

(52) U.S. Cl.
CPC ............... *F21V 21/084* (2013.01); *A42B 3/044* (2013.01); *A61B 5/6814* (2013.01); *F21W 2131/20* (2013.01); *A61B 2019/262* (2013.01)
USPC ......................................... 362/105; 362/572

(58) Field of Classification Search
CPC ............ F21V 21/084; A61B 2019/262; A61B 5/6814; A61B 3/044; A61B 3/286; F21W 2131/20; F21W 2131/202; A42B 3/044; A42B 3/286
USPC ................... 362/105, 572–575; 361/694–697
See application file for complete search history.

(56) References Cited

U.S. PATENT DOCUMENTS 2,437,748 A    3/1948   Malcom
3,047,876 A    8/1962   Malcom
(Continued)

FOREIGN PATENT DOCUMENTS

EP    2 641 018    9/2013
JP    08/288205    11/1996
(Continued)

OTHER PUBLICATIONS

"LED Surgical Headlight Technical Review," Welch Allyn, Oct. 22, 2009.

(Continued)

*Primary Examiner* — David J Makiya
(74) *Attorney, Agent, or Firm* — Jenkins, Wilson, Taylor & Hunt, P.A.

(57) ABSTRACT

Wearable headlight devices and related methods are provided and can include a luminaire that can include a housing having a luminaire vent therein for receiving cooling air and a light source contained within the housing. An air moving device can be located outside of the luminaire for facilitating cooling air intake through the luminaire vent. An exhaust tube can be connected to the luminaire and the air moving device to facilitate air flow of the cooling air between the luminaire and the air moving device.

32 Claims, 10 Drawing Sheets

(56) References Cited

U.S. PATENT DOCUMENTS

| | | |
|---|---|---|
| 3,470,570 A | 10/1969 | Christiansen |
| 3,555,560 A | 1/1971 | Rascke |
| 3,745,993 A | 7/1973 | Feinbloom |
| 3,763,495 A | 10/1973 | De Angelis |
| 3,947,676 A | 3/1976 | Battilana et al. |
| 3,992,722 A | 11/1976 | Rhee |
| 4,130,902 A | 12/1978 | Mackenroth, III et al. |
| 4,593,683 A | 6/1986 | Blaha |
| 4,729,499 A | 3/1988 | Martin |
| 4,942,628 A | 7/1990 | Freund |
| D337,838 S | 7/1993 | Van der Bel |
| 5,608,917 A | 3/1997 | Landis et al. |
| D383,229 S | 9/1997 | Kiichiro |
| 5,774,271 A * | 6/1998 | Lagerway et al. ............ 359/649 |
| D406,371 S | 3/1999 | Van der Bel |
| 6,341,382 B1 | 1/2002 | Ryvin et al. |
| 6,567,993 B2 | 5/2003 | Robertson |
| D503,499 S | 3/2005 | Howard et al. |
| 6,890,086 B2 | 5/2005 | Shiu |
| 6,955,444 B2 | 10/2005 | Gupta |
| 6,966,074 B2 | 11/2005 | Huh |
| 6,999,318 B2 | 2/2006 | Newby |
| 7,134,763 B2 | 11/2006 | Klootz |
| 7,192,151 B2 * | 3/2007 | Clupper et al. ............... 362/105 |
| D539,952 S | 4/2007 | Iranyi et al. |
| 7,314,294 B1 * | 1/2008 | Moore .......................... 362/373 |
| 7,314,300 B1 * | 1/2008 | Dorr et al. ..................... 362/581 |
| 7,618,159 B2 * | 11/2009 | Tamburrino et al. .......... 362/321 |
| 2006/0245175 A1 | 11/2006 | Heine et al. |
| 2006/0285315 A1 | 12/2006 | Tufenkijan et al. |
| 2006/0285316 A1 * | 12/2006 | Tufenkjian et al. ........... 362/105 |
| 2007/0220649 A1 | 9/2007 | Huh |
| 2009/0116252 A1 | 5/2009 | Kille et al. |
| 2009/0161348 A1 * | 6/2009 | Spartano et al. .............. 362/105 |
| 2009/0225534 A1 | 9/2009 | Thomas et al. |
| 2009/0229041 A1 | 9/2009 | Tufenkijan |
| 2011/0160541 A1 | 6/2011 | Koyama et al. |

FOREIGN PATENT DOCUMENTS

| | | |
|---|---|---|
| JP | 2006/147373 | 6/2006 |
| JP | 2008/186694 | 8/2008 |
| JP | 2008/198468 | 8/2008 |
| JP | 2008/227127 | 9/2008 |
| JP | 2010/046566 | 3/2010 |
| WO | WO 2010/007785 | 1/2010 |
| WO | WO 2012/068116 | 5/2012 |

OTHER PUBLICATIONS

International Search Report and Written Opinion for PCT/US2011/060799 dated Mar. 29, 2012.

Petzl Elios Vision Helmet, Spring 2007 Moosejaw Website; http://www.moosejawlowdown.com/moosejaw . . . (3 pages).

Non-Final Office Action for U.S. Appl. No. 12/048,050 dated Mar. 28, 2011.

Australian Examination Report for Application No. 2011329035 dated Apr. 14, 2014.

Japanese Office Action for Application No. 2013/539950 dated Apr. 15, 2014.

* cited by examiner

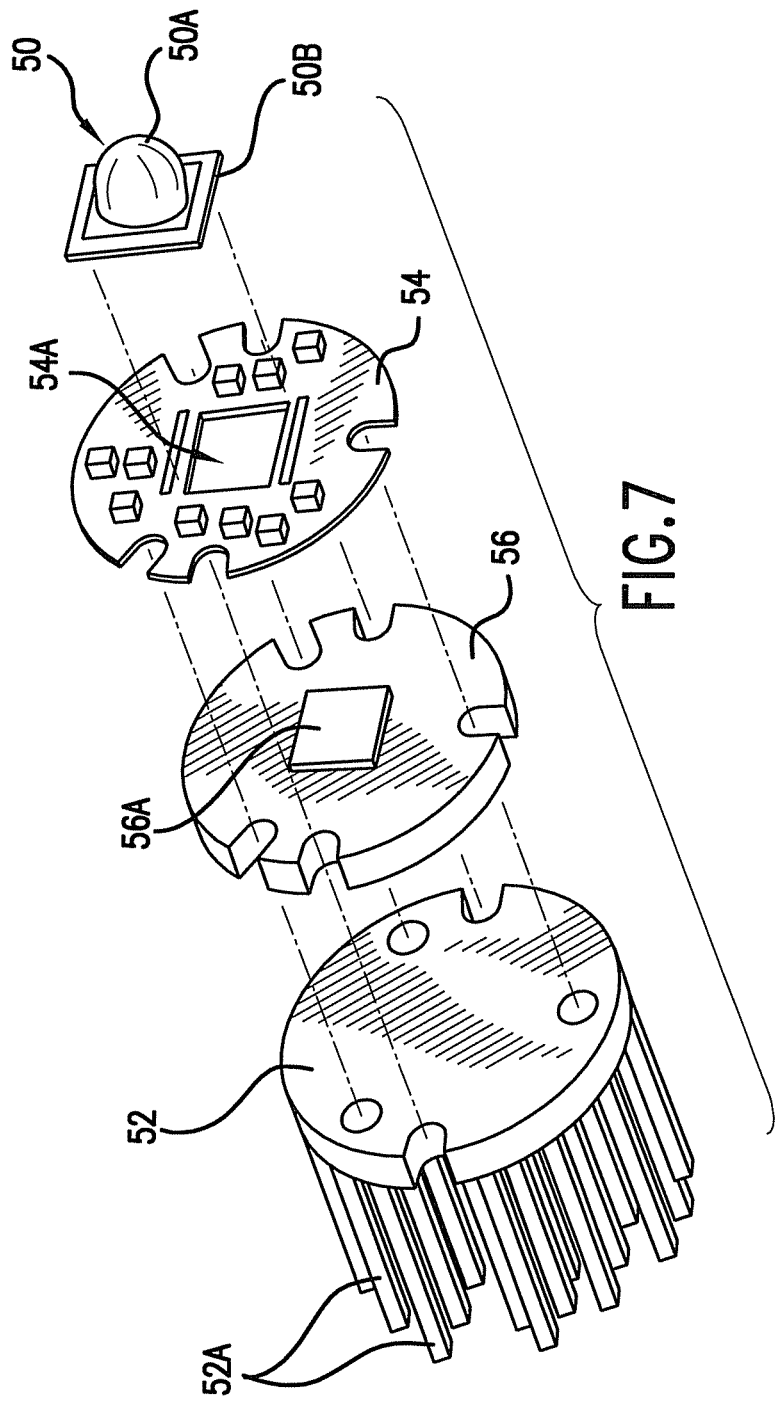

WEARABLE HEADLIGHT DEVICES AND RELATED METHODS

CROSS REFERENCE TO RELATED APPLICATIONS

The presently disclosed subject matter claims the benefit of and priority to U.S. Provisional Patent Application Ser. No. 61/414,739, filed Nov. 17, 2010, the disclosure of which is incorporated herein by reference in its entirety.

TECHNICAL FIELD

The subject matter disclosed herein relates generally to headlights to be worn on a user's head to provide supplemental light. More specifically, the subject matter disclosed herein relates to wearable headlight devices and methods utilizing a light source such as a light emitting diode ("LED") devices.

BACKGROUND

Existing surgical headlights require a significant amount of light, approximately 400 lumens minimum for example, to provide sufficient illumination for a surgeon during a typical procedure. Surgical headlights must also be lightweight and typically weigh less than 400 grams for example, so that neck and head fatigue is minimized. To satisfy both conditions, the following architecture is utilized by most manufacturers: a remote Xenon light source is optically coupled to a fiber optic cable that transmits light energy to the luminaire which is mounted on a head wearable portion. The luminaire focuses the light and produces a spot of bright light typically 120 mm in diameter at 400 mm away from the luminaire. There are several disadvantages of this architecture. First, the surgeon is tethered to a large light source, which constrains his or her movement. Second, the light source takes up valuable room in the operating room. Third, the light source typically consumes about 380 W of power. Fourth, the Xenon lamps are expensive and must be replaced periodically. Typical life is about 650 hours. Fifth, fiber optic cables are expensive, fragile and must be replaced periodically. Sixth, additional optical components and assemblies may be required for filtering out UV and IR.

LEDs are semiconductor devices that emit light by application of electrical power (watts). White light LED technology has advanced to the point where one LED can produce as much as 1200 lumens. This makes it a feasible light source for a surgical headlight luminaire. An LED surgical headlight can achieve light output and weight requirements. A problem however with LEDs is that they generate heat that must be addressed, and one of the major challenges LEDs pose in many applications is dissipating and/or removing the heat generated by an LED. Excess heat must be removed so that the semiconductor junction temperature does not exceed recommended maximum temperature. In addition, as the junction temperature of the LED rises, the efficiency also drops. LED light output is limited by its maximum heat junction temperature, so to increase light output without damaging the LED or reducing its operating efficiency, heat must be transferred quickly and efficiently.

There remains a need for improved headlight devices and methods that satisfy weight and light output expectations.

SUMMARY

It is an object of the present disclosure to provide novel headlight devices and methods, such as for surgical procedures for example, where the devices are efficiently cooled to maintain light output, efficacy (efficiency), reliability and life. It is another object to provide compact LED luminaire optics with enhanced light output.

A few objects of the presently disclosed subject matter having been stated hereinabove, and which are achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIG. 7 illustrates an exploded view of an embodiment of a light-emitting diode package in accordance with the subject matter disclosed herein;

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment may be used in another embodiment to yield still a further embodiment. It is intended that the present subject matter cover such modifications and variations.

As noted above, improved headlights, such as wearable surgical headlights, and methods are disclosed herein that can utilize light emitting devices, such as for example light emitting diodes (LEDs). The use of LEDs in a wearable headlight device as disclosed herein has advantages over conventional Xenon based wearable headlights. For example and as disclosed in further detail herein, an LED headlight can be powered by a portable battery pack worn by the user, thus allowing freedom of movement. Also, an LED headlight does not require a remote light source since the LED can be integrated into the luminaire. Additionally, an LED headlight can consume for example only about 5% (20 W) of power utilized by a Xenon light source. LED life can advantageously be for example up to 50,000 hours depending upon drive current and operating temperature. Finally, LED headlights do not require fiber optic cables, and white light LEDs advantageously do not generate significant amounts of UV or IR.

Figure 1:
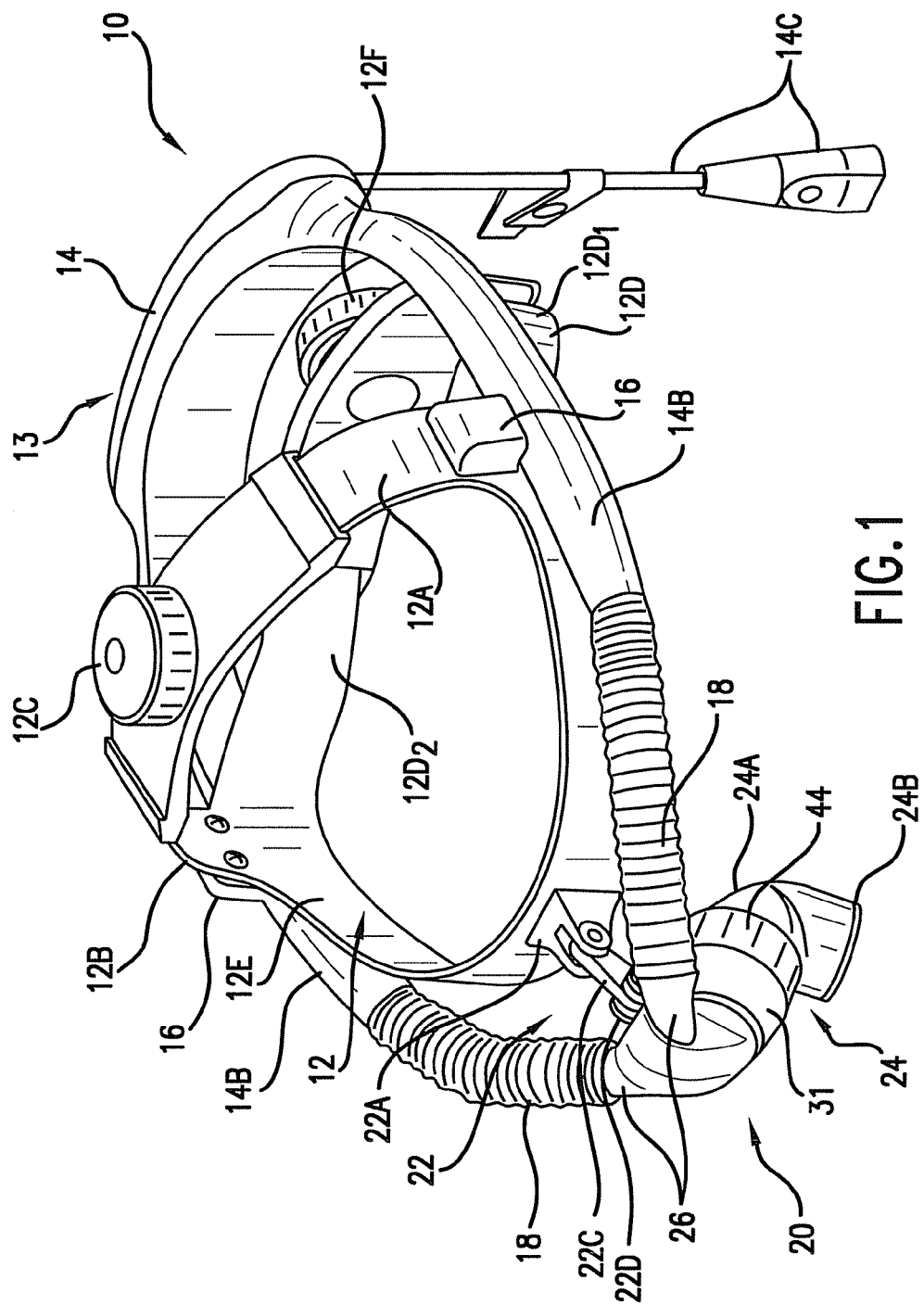
FIG. 1 illustrates a perspective view of an embodiment of a headlight device in accordance according to an embodiment of the subject matter disclosed herein.
Figure 2:
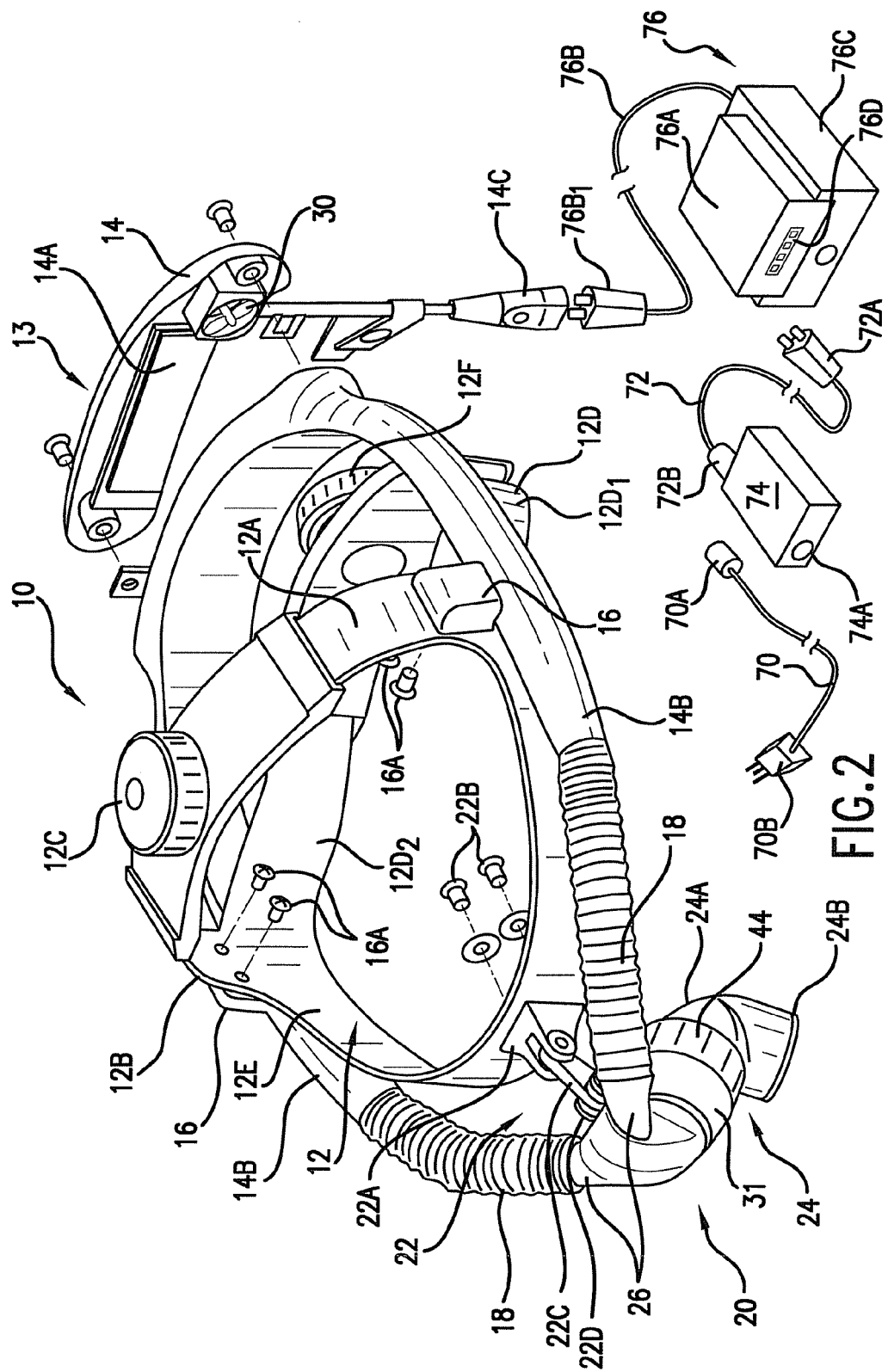
FIG. 2 illustrates an exploded view of the embodiment of the headlight device according to FIG. 1.

FIGS. 1 and 2 show a wearable headlight device generally designated 10 in accordance with some embodiments of the subject matter disclosed herein. Headlight device generally designated 10 can comprise a luminaire 20. Headlight device 10 can optionally comprise a head wearable portion generally designated 12 with luminaire 20 attached to head wearable portion 12 as shown in FIGS. 1 and 2. Headlight device 10 is thus a medical device that can for example and without limitation be worn on a surgeon's head to provide supplemental light for surgical and medical procedures, whenever supplemental illumination, especially shadow-free coaxial illumination, is desired or required to facilitate a surgical or medical procedure. The intended user for headlight device 10 can be, for example, physicians, surgeons and other trained, qualified medical professionals providing medical or surgical assistance. Intended patients can be any individuals undergoing surgical or medical procedures where additional illumination is deemed necessary by a practitioner performing a procedure.

Head wearable portion 12 can be plastic and can be configured to attach to and securely position one or more devices and can be adapted to be worn on a user's head. It is commonly configured and referred to as a headband. Head wearable portion 12 can comprise overhead straps 12A and 12B that can form an arch that can rest upon a top portion (or crown) of the head of the user. Head wearable portion 12 can be adjustable to fit the head of the user. For example, adjuster 12C, such as a ratchet knob, can be used to adjust the position of overhead straps 12A and 12B relative to one another. For instance, if adjuster 12C is rotated in a first direction, then overhead straps 12A and 12B can be pulled closer together to accommodate a smaller crown of the head. If the adjuster 12C is rotated in a second direction opposite the first direction, then overhead straps 12A and 12B can be pushed away from each other to accommodate a larger crown of the head.

Head wearable portion 12 can comprise a rear headband portion 12D and a front headband portion 12E. As shown in FIGS. 1 and 2, rear headband portion 12D can comprise two straps $12D_1$ and $12D_2$ and rear headband portion 12D can also be adjustable. Rear headband portion 12D can comprise an adjuster 12F that can be used to adjust the position of straps $12D_1$ and $12D_2$ relative to one another to adjust to the head size of the user. For instance, if adjuster 12F is rotated in a first direction, then straps $12D_1$ and $12D_2$ can be pulled closer together to accommodate a smaller head. If the adjuster 12F is rotated in a second direction opposite the first direction, then straps $12D_1$ and $12D_2$ can be pushed away from each other to accommodate a larger head. Thus, with the adjustability for both the crown and the head size of the user, head wearable portion 12 can be comfortably conformed to the user's head. Head wearable portion 12 can utilize replaceable/disposable foam pad sets for front headband portion 12E, rear headband portion 12D, and overhead straps 12A and 12B for respectively padding the forehead, back and crown of the user. Headband pads can attach to the headband via a hook and loop system.

A luminaire generally designated 20 can be located along front headband portion 12E of head wearable portion 12. For example, a connector generally designated 22 can be used to hold luminaire 20 to front headband portion 12E so that luminaire 20 can be positioned between the eyes of the head of the user. Connector 22 can include a connector base 22A that can be rigidly attached to front headband portion 12E by fasteners 22B shown for example in FIG. 2. A connector link 22C can be rotatably connected to connector base 22A on one end and rotatably connected to a connector receiver 22D on luminaire 20. Since connector receiver 22D can be moved relative to the connector base 22A through the rotatable connections with connection link 22C, luminaire 20 can be moved relative to head wearable portion 12 and when in use, relative to the head of the user. In some embodiments, one or more links can be used. For example, connector link 22C can be rotatably connected to connector base 22A on one end and rotatably connected to a second link (not shown) that is rotatably connected to connector receiver 22D on luminaire 20. In such embodiments, increased rotation of luminaire 20 may be achievable. The position and orientation of luminaire 20 can thus be adjustable with force by the user but remain fixed during intended use.

Luminaire 20 can also comprise a luminaire housing 24 to contain the components of luminaire 20. Luminaire housing 24 can comprise one or more venting tubes such as venting tubes 26 at a top end that can be distal from an outer lens 42 (FIG. 3) of luminaire 20. Venting tubes 26 can be used to vent or express hot air out of luminaire housing 24. For example, head wearable portion 12 as shown in FIG. 2 particularly can also comprise a controller 13 that can comprise a controller housing 14 that can hold a controller board 14A. Controller housing 14 can also house an air moving device 30, such as a fan, that can create an airflow. Thus, an active cooling system for headlight device 10 can include one or more exhaust tubes 18, which can be or can include some flexible portion or portions, and controller housing 14 with air moving device 30, such as an exhaust fan. Controller 13 can also be located in any other suitable location and even not attached to head wearable portion 12. In some embodiments, a single exhaust tube 18 can be provided to facilitate the airflow through and away from luminaire 20. For example, a single exhaust tube 18 can run along a side or over a top portion of head wearable portion 12.

While headlight device 10 is described with a head wearable portion that is separate from exhaust tubes 18, in some embodiments, the exhaust tubes, such as exhaust tubes 18, can comprise the head wearable portion. In such embodiments, exhaust tubes 18 can be rigid enough to hold luminaire 20 and control housing 14 on a head of a user. Luminaire 20 can be connected to exhaust tubes 18 to permit airflow to pass from luminaire 20 to exhaust tubes 18, while also allowing luminaire 20 to be adjustable relative to exhaust tubes 18.

Controller housing 14 can extend outward from head wearable portion 12 above rear headband portion 12D and can be constructed, for example, of Radel® high temperature, UL94 VO engineering resin. Controller housing 14 can be the just the back portion in which controller board 14A resides or both the front and back portions shown in FIG. 2. Controller housing 14 can include air flow tubes 14B that can be rigid and can be in fluid flow communication with air moving device 30. Control housing 14 can be secured to head wearable portion 12 in a variety of manners. In the embodiment shown in FIGS. 1 and 2 for example, connectors 16 that can include fasteners 16A can be used to secure controller housing 14 to overhead straps 12A and 12B. As shown, connectors 16 can be located respectively above a portion of air flow tubes 14B. The one or more venting tubes 26 can be connected to air flow tubes 14B by exhaust tubes 18. Exhaust tubes 18 can be flexible to permit movement of luminaire 20 relative to head wearable portion 12. Thus, through an airflow created by air moving device 30, hot air can be pulled from luminaire housing 24 through the one or more venting tubes 26 and exhaust tubes 18 to air flow tubes 14B. From air flow tubes 14B, the air is pulled out and through air moving device 30.

Controller housing 14 can also include a power connector 14C that can be connected to a power supply to supply power to control board 14A and air moving device 30 in controller housing 14. Further, connector 14C can also supply power to luminaire 20. Both the cooling system and the power supply system are described further below.

Figure 3:
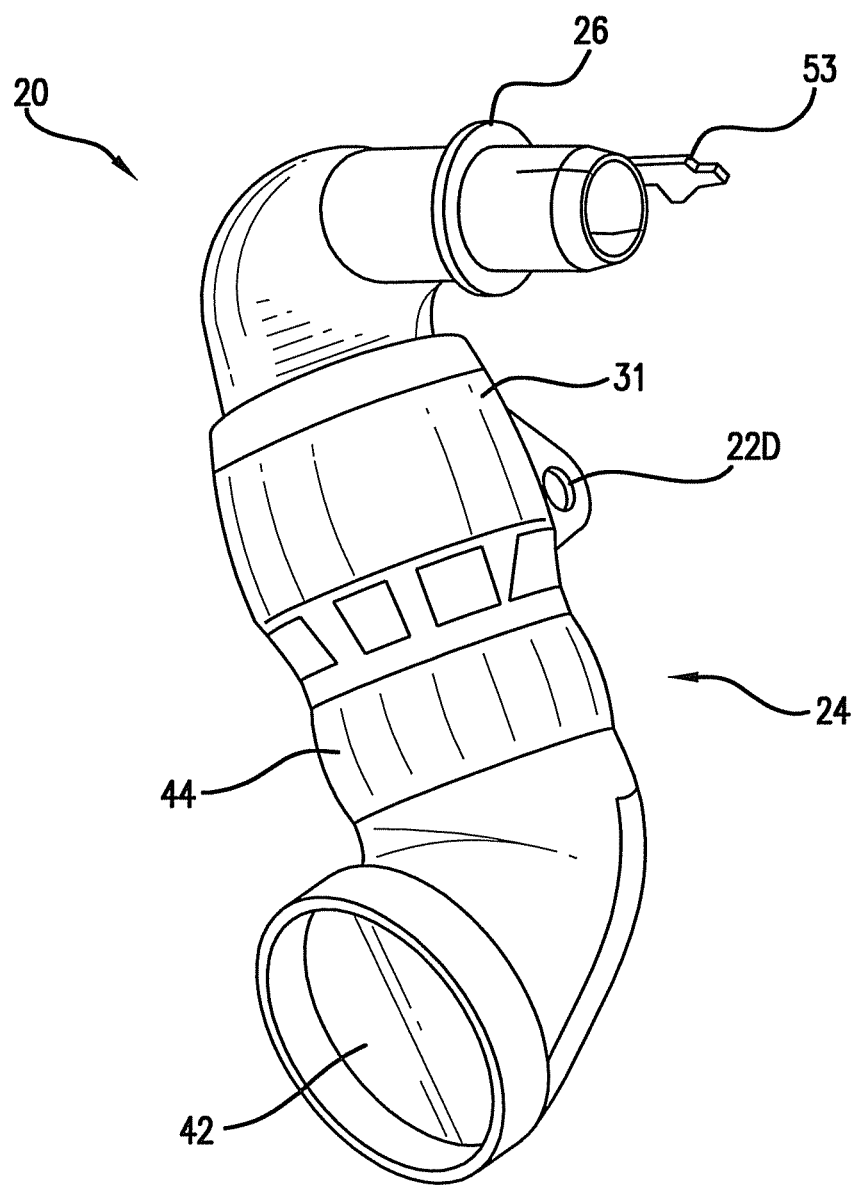
FIG. 3 illustrates a perspective view of an embodiment of an LED luminaire in accordance with the subject matter disclosed herein.

As shown in FIG. 3, luminaire 20 can comprise outer lens 42. As shown in FIGS. 1, 2, 3, 4A and 4B, luminaire 20 can also comprise an iris controller 44 which can be rotatable relative to luminaire housing 24 for controlling the degree of dilation or constriction of an iris 60 (see FIGS. 5A, 5B, 6, and 9) within luminaire 20. Iris controller 44 can comprise an exterior wheel to control the opening of iris 60. Iris controller 44 can have an instrument feel provided by oring or wave spring, for example, to enhance the gripping of iris controller 44. Luminaire housing 24 can also comprise an angled back 24A that can reside below the portion of the housing in which LED light source 50 described further below resides. A mirror (FIG. 9) can reside on an interior portion of angled back portion 24A to angle the light generated by LED light source 50. Luminaire housing 24 can also comprise an outer lens housing 24B that extends outward from luminaire housing 24 and angled back portion 24A. Outer lens housing 24B can have outer lens 42 reside therein.

Figure 4A:
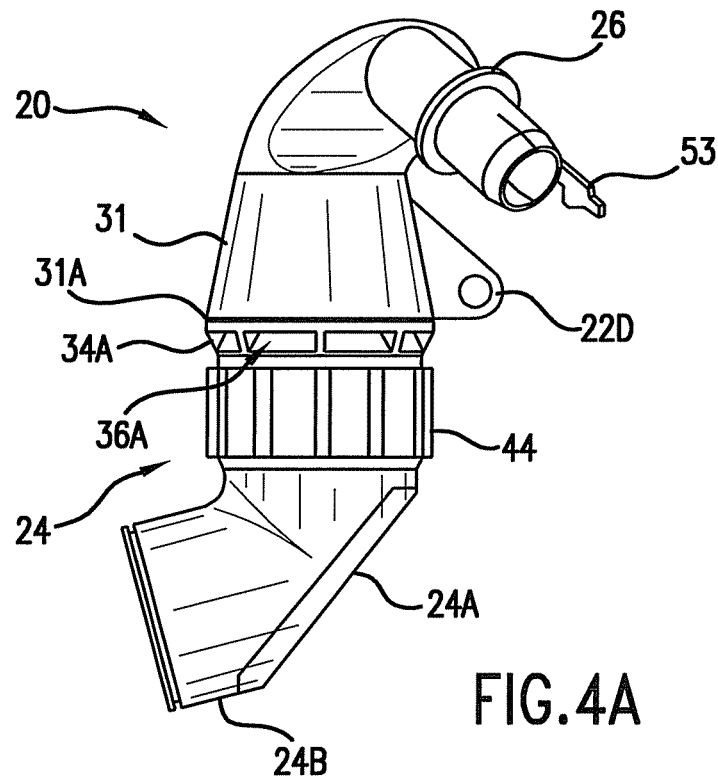
FIGS. 4A and 4B illustrate additional LED luminaire embodiments in accordance with the subject matter disclosed herein.
Figure 4B:
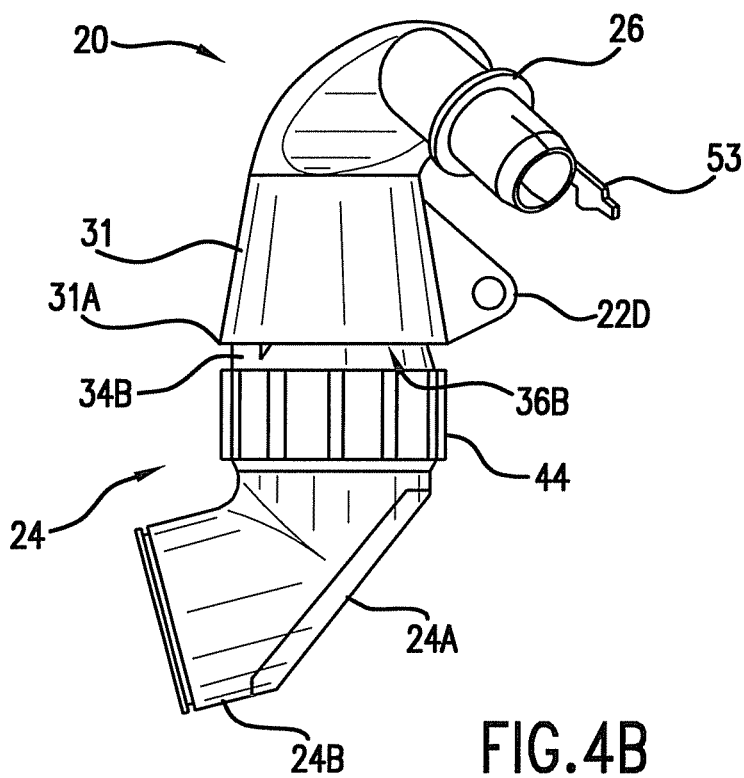

Luminaire housing 24 can comprise a suspension ring 31 that can include a luminaire skirt 31A. Connector receiver 22D can extend from suspension ring 31 to provide connection to head wearable portion 12 as described above. Luminaire housing 24 can also comprise luminaire vents. Luminaire vents can be constructed in many ways as apparent to a person skilled in the art. For example, luminaire housing 24 can include a vent ring 34A (see FIG. 4A) or 34B (see FIG. 4B). In FIG. 4A, vent ring 34A can have luminaire vents 36A that are visible. Alternatively, as illustrated in FIG. 4B, vent ring 34B can have luminaire vents generally designated 36B that can be constructed so luminaire skirt 31A covers the luminaire vents 36B so that an individual viewing the front of the luminaire cannot see vents 36B. Above the suspension ring 31, luminaire housing 24 can also comprise a vent tube portion that can include one or more venting tubes 26 as described previously.

Figure 5A:
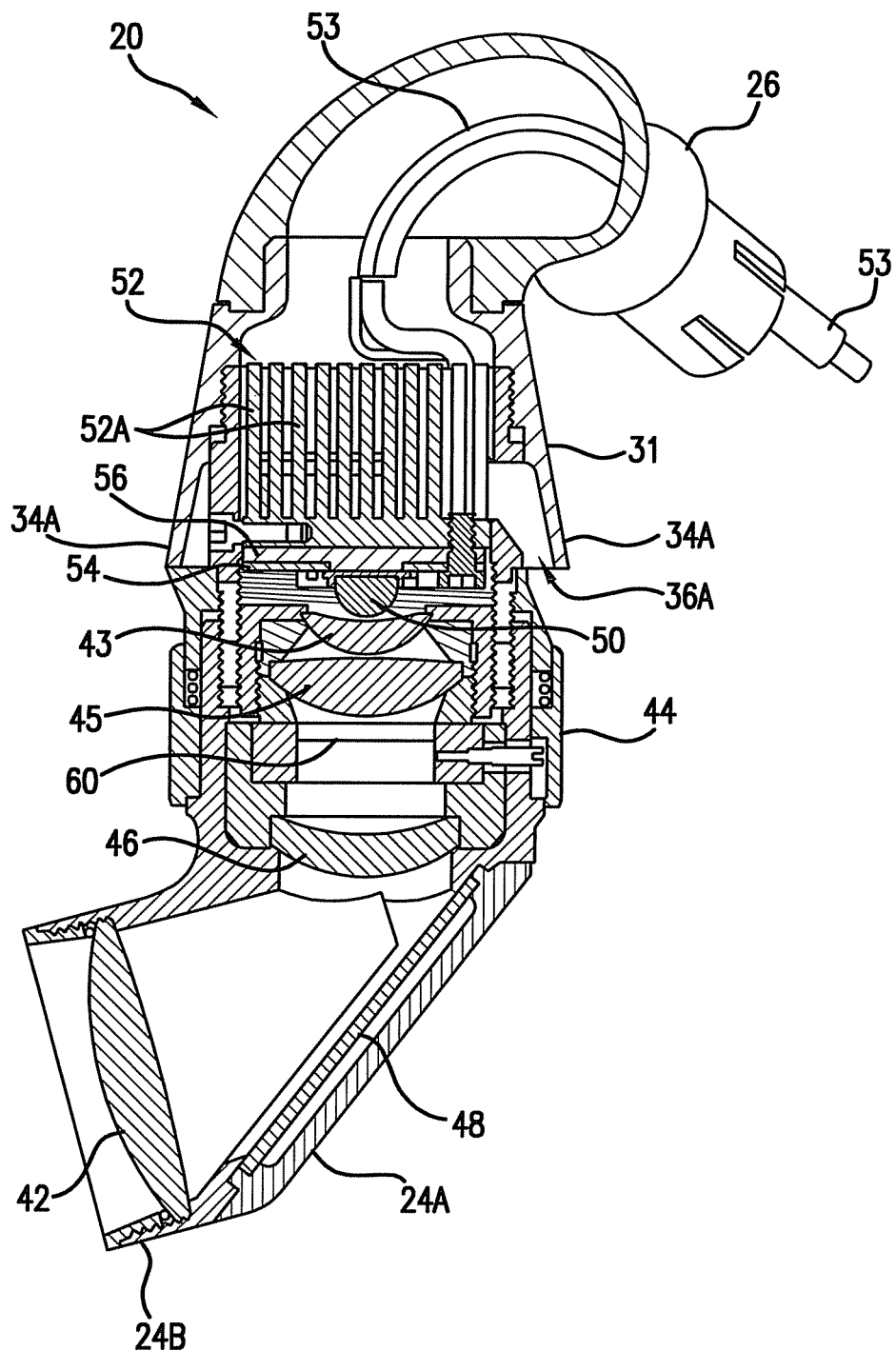
FIGS. 5A and 5B illustrate cross-sectional views along the length of the embodiments of the LED luminaire of FIGS. 4A and 4B to illustrate the internal configurations.
Figure 5B:
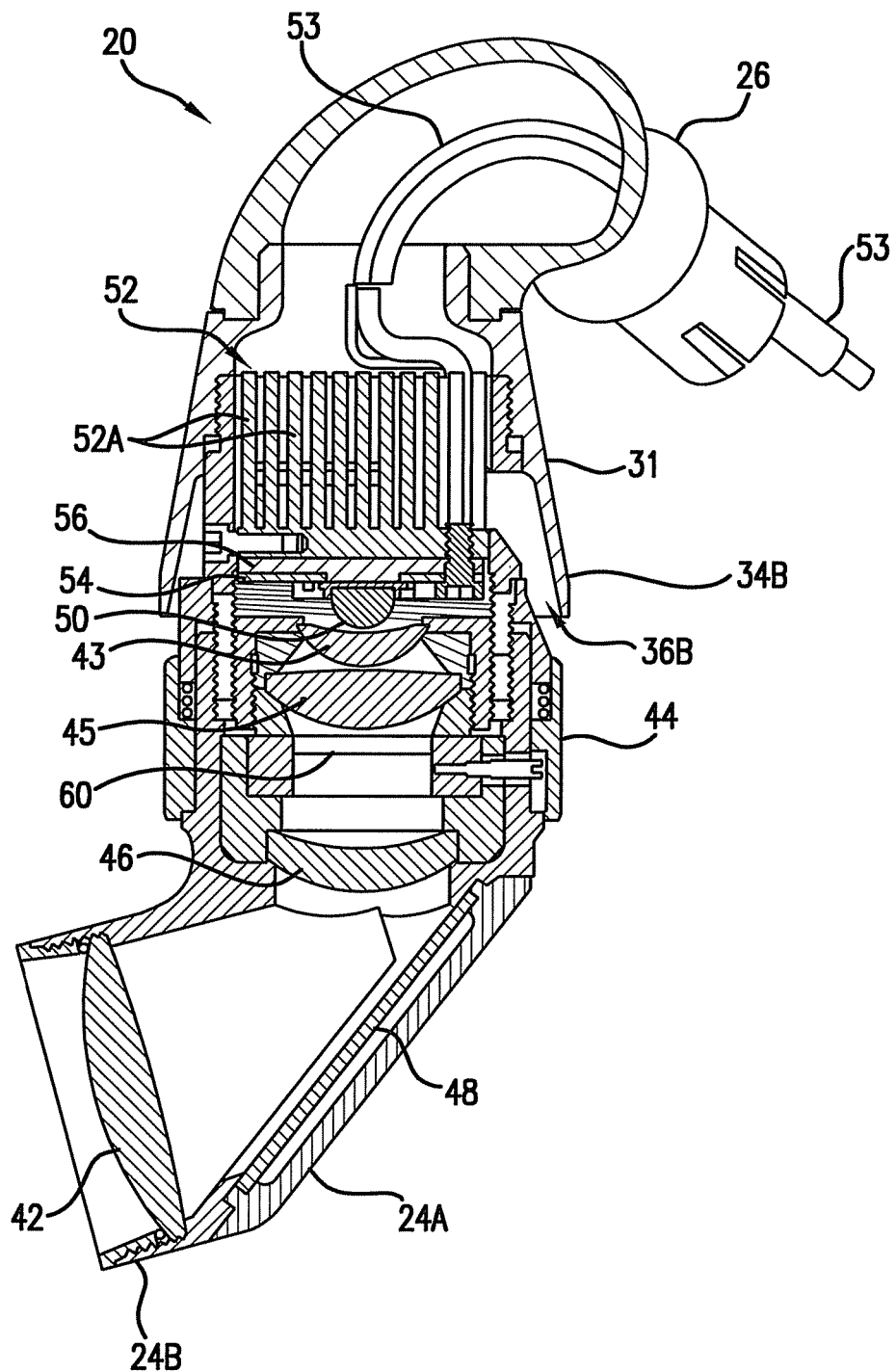
Figure 6:
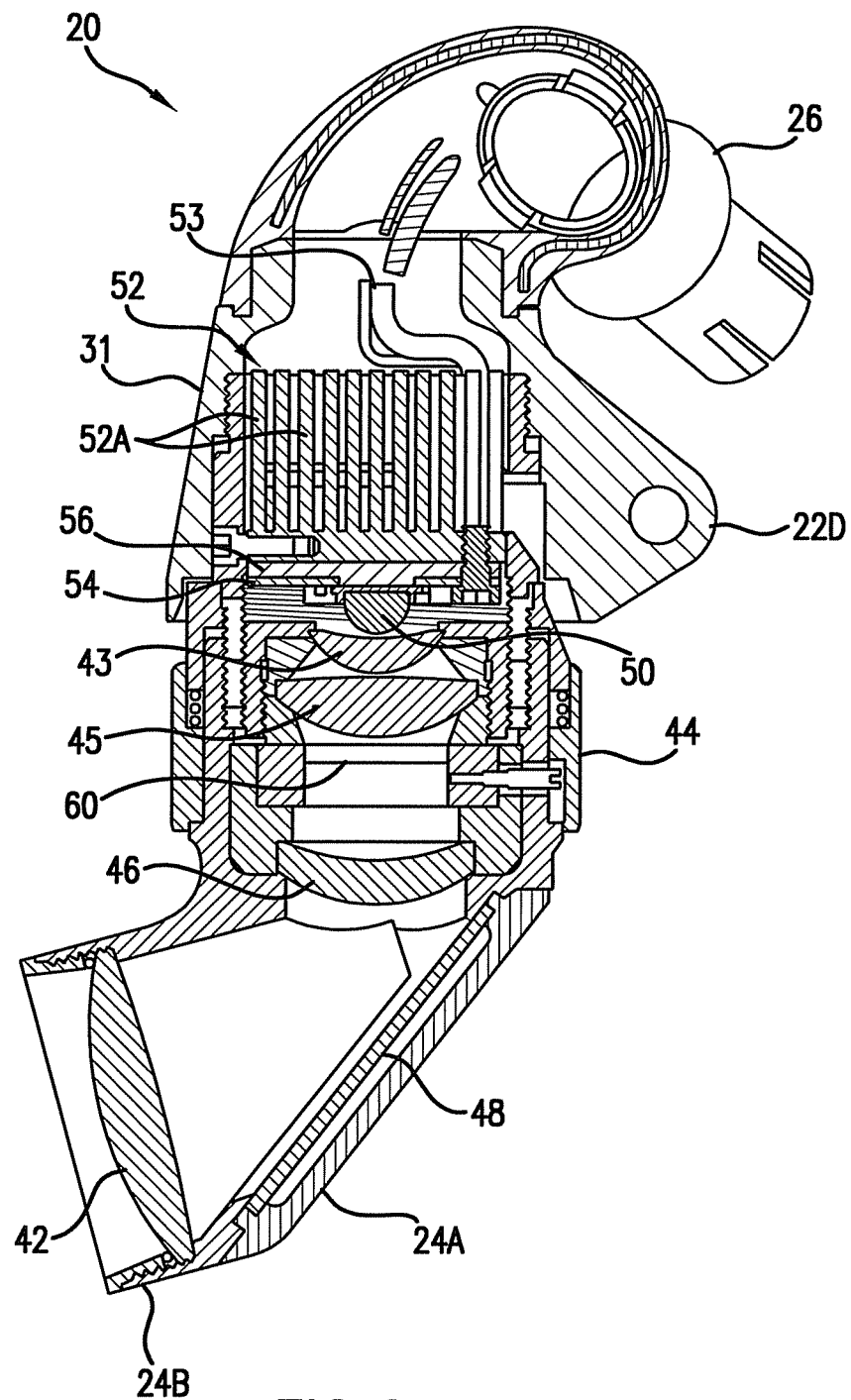
FIG. 6 is a schematic cross-sectional view of an internal configuration of the luminaire embodiment of FIG. 4B.

As shown in FIGS. 5A, 5B and 6, luminaire 20 can comprise a light source 50, a heat sinking device, or heat sink 52, and optics 40 (see FIG. 9 including iris control 44 in FIGS. 5A, 5B and 6) within the luminaire housing. Light source 50 can comprise one or more different or identical light sources, such as light bulbs, light-emitting diodes (LEDs), lasers, and the like. In the embodiments shown for illustration purposes, light source 50 can comprise an LED light source, which can comprise one or more LEDs. Heat sink 52 can reside in a heat sinking chamber in suspension ring 31 and can be in thermal communication with LED light source 50. For example, heat sink 52 can be in direct contact with LED light source 50 or a thermal conductive material may reside between LED light source 50 and heat sink 52.

As discussed above, the cooling system for luminaire 20 can comprise luminaire vents 36A, 36B or intake vents located within luminaire housing 24. Luminaire vents 36A, 36B can receive cooling air that can pass over heat sink 52 and can be discharged from luminaire housing 24 through the one or more venting tubes 26 to a location outside of and away from luminaire 20 and heat sink 52. As described above, air can be pulled and flow through luminaire vents 36A, 36B, over the heat sink to dissipate and remove heat through venting tubes 26 and exhaust tubes 18. From there, the air that has now been heated by the heat sink can be pulled and flow through air flow tubes 14B and through air moving device 30. Air moving device 30 can generate the air flow that pulls air through the luminaire vents 36A, 36B and through air moving device 30, expelling the heated air away from the head of the user. In some embodiments of the present subject matter, LED cooling can achieved by an air moving device 30 that comprises, for example, a Sunon® 1 Watt fan. Controller board 14A can provide a thermal cut out that can shut down LED light source 50 if it overheats as described further below. The brightness of LED light source 50 can be controlled by controller board 14A varying the current supplied to LED light source 50.

As described previously, controller housing 14 can also have controller board 14A residing therein which can control and/or adjust the operation of air moving device 30 and light source 50. For example, controller housing 14 can house a thermostat, a switch for a power supply, and switch for air moving device 30. In such an embodiment, where the thermostat is in the controller housing 14, a temperature sensor can be disposed in proximity to light source 50. In one aspect, a thermostat T can be in proximity of the light source 50 as shown schematically in FIG. 10. Wiring 53 can pass from controller board 14A and connector 14C through air flow tubes 14B, exhaust tubes 18, and venting tubes 26 to light source 50 to supply power to LED light source 50 and to provide communication to control and adjust the light output from light source 50.

Figure 8A:
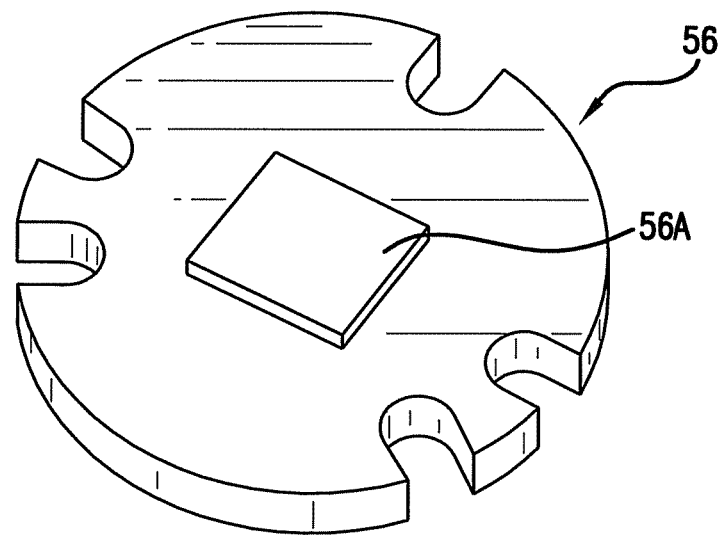
FIG. 8A illustrates a perspective view of an embodiment of a thermal conductive board that can be laminated to an embodiment of a printed circuit board ("PCB") used in the embodiment of the light-emitting diode package according to FIG. 7.
Figure 8B:
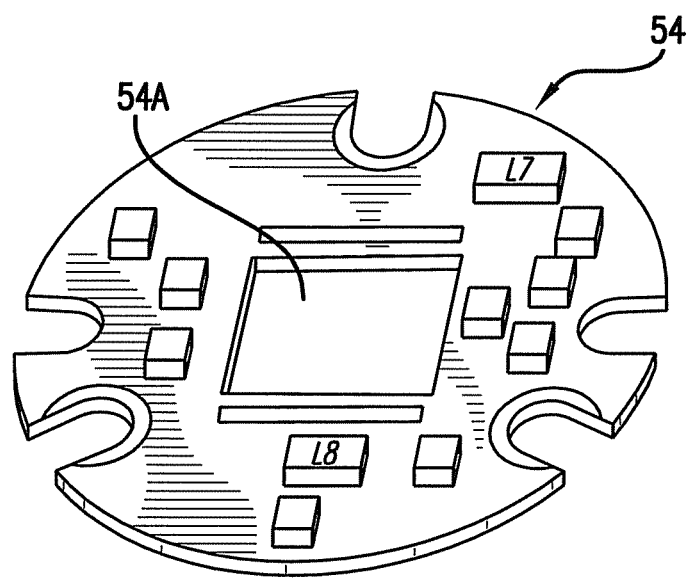
FIG. 8B illustrates a perspective view of an embodiment of the PCB used in the embodiment of the light-emitting diode package according to FIG. 7.

As shown in FIGS. 7, 8A and 8B, LED light source 50 can comprise an LED lens 50A that can resides and be disposed over a mounting pad that can include electrical traces and the diodes (not shown) that will emit light when powered. The mounting pad and electrical traces can reside on a substrate that can form an LED base, or slug, 50B. A printed circuit board (PCB) 54 can be electrically connected to LED 50. PCB 54 can have an opening 54A therethrough. A thermal conductive board, or heat sink pad, 56 can be laminated to PCB 54. Thermal conductive board 56 can comprise a protrusion 56A that can extend up through opening 54A in PCB 54 and can be soldered directly to LED base 50B. In some embodiments, thermal conductive board 56 and protrusion 56A can be a conductive metal such as copper for example. Thermal conductive board 56 can be secured to heat sink 52 in a manner that will facilitate thermal transfer from thermal conductive board 56 to heat sink 52.

A method of heat transfer from LED light source 50 that can be used in headlight device 10 to efficiently transfer heat energy from LED 50 can be conduction from LED base 50B. Light output from LED light source 50 can be limited by its maximum heat junction temperature. To increase light output without damaging LED light source 50 or reducing its operating efficiency, heat can be transferred quickly and efficiently by reducing the thermal resistance at LED base 50B so that the heat transfer rate can be increased. Copper protrusion 56A can extend up through opening 54A in PCB 54 and can be soldered directly to LED base 50B, thereby greatly reducing thermal resistance. By soldering LED base 50B directly to copper protrusion 56A that extends from copper thermal conductive board 56, the thermal resistance can be greatly reduced. In some embodiments, LED light source 50 and heat sink 52 located inside of the luminaire can be in direct thermal contact with each other. To provide more surface area to remove heat from heat sink 52, heat sink 52 can comprise a plurality of projections 52A that extend from a back surface of heat sink 52 away from LED light source 50.

PCB 54 is shown in FIGS. 7, 8A and 8B as two pieces for clarity. Thermal conductive board 56 can be a copper piece and can be laminated to board 54, which can be a polyamide or FR4 board using epoxy laminating process common in the PCB industry. Protrusion 56A can extend up through opening 54A in PCB 54 and soldered directly to LED base 50B of LED light source 50. Direct soldering of LED solder pad to copper core board may yield a low thermal resistance, and thus a low junction temperature. This thermal cooling design enables LED light source 50 to generate more lumens in response to receiving more cooling, as compared to an LED receiving cooling from a heat sink that is not in direct thermal contact with the LED.

Figure 9:
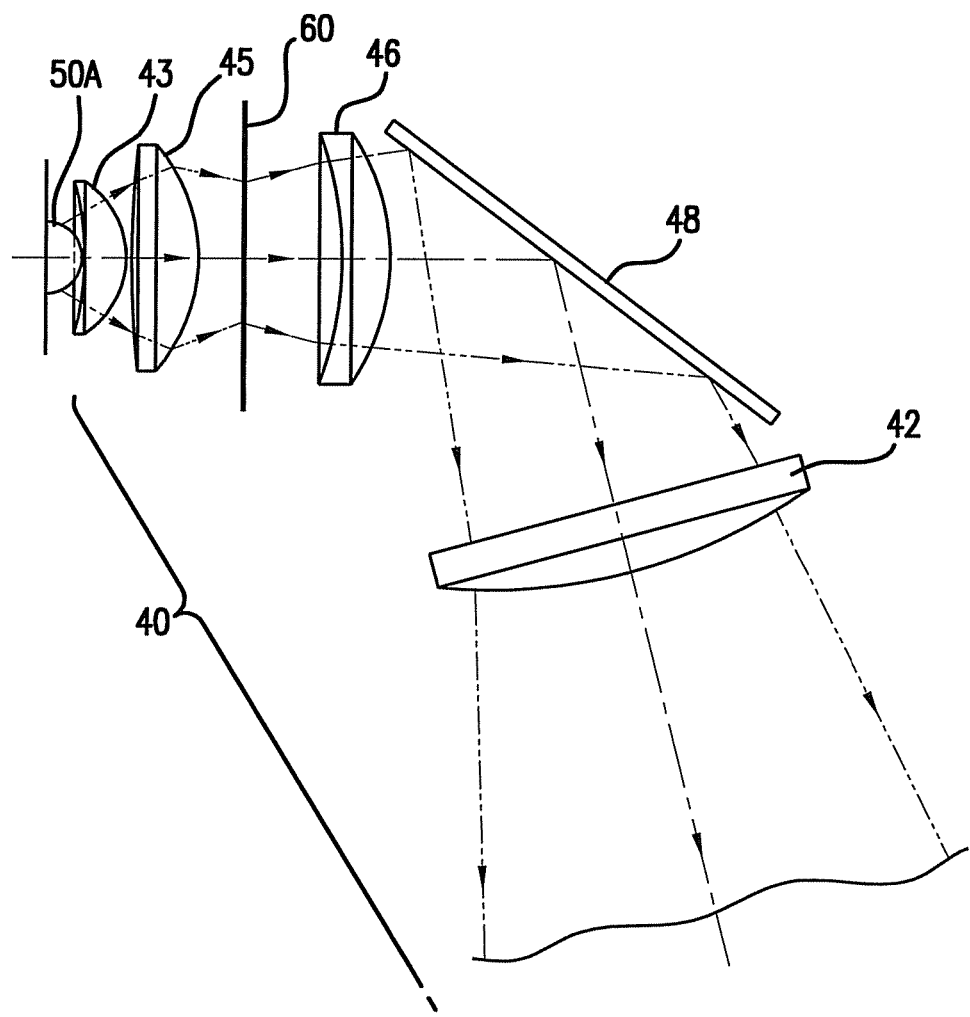
FIG. 9 illustrates a perspective view of an embodiment of an optical construction or configuration that can be used in an embodiment of a luminaire in accordance with the subject matter disclosed herein.

Optics 40, shown in FIG. 9, can provide an arrangement of optical components within the luminaire designed to efficiently capture light from LED light source 50 and to project the light with high quality characteristics along an axis that is at least proximate to being parallel to the line of sight of the wearer. These high quality characteristics can include projection of a pre-determined and adjustable light spot size at a particular distance from the wearer that can be substantially free of cosmetic defects (artifacts) and that can be projected in a direction and with a well-defined edge to limit shadowing and collateral glare.

FIGS. 5A, 5B, 6 and 9 illustrate LED luminaire optics 40 and its components in accordance with an embodiment of the subject matter disclosed herein. Optics 40 can be based on the principle of Koehler illumination and can comprise one or more condensing lens 43, 45 and one or more objective lens 42, 46 with iris 60 and folding mirror 48 placed in between. In the embodiment shown in FIGS. 5A, 5B, 6 and 9, a first condensing lens 43 is positioned proximate to lens 50A of LED light source 50 to maintain a compact and cost effective format. First condensing lens 43 can be constructed from high index glass. A second condensing lens 45 can be placed below and proximate to first condensing lens 43 to provide a doublet of elements. Second condensing lens 45 can also comprise high index glass, for example, Schott LaSFN 31 or optical equivalent. To maximize collection efficiency, the first condensing lens 43 can be placed in close proximity to the LED dome or lens 50A and can be shaped as a meniscus lens. The optical design can feature a high curvature meniscus lens located a distance, for example, of about 0.25 mm, from the LED dome for maximum light collection. The function of condensing lenses 43, 45 can be to efficiently collect light (represented by the lines and arrows in FIG. 9) from LED light source 50 and back-illuminate an iris 60 with a beam that has a uniform light distribution and can be properly sized to an opening in iris 60.

To maintain a compact cost effective optics format, objective lenses can comprise first objective lens 46 and second (or outer) objective lens 42 to provide a split doublet. The light can pass through iris 60 toward first objective lens 46 which directs or focuses the light toward folding mirror 48. First objective lens can comprise high index glass as well. The light can reflect off of folding mirror 48 at an angle toward outer objective lens 42 which can provide a light beam focused in the manner desired by the user. Second, or outer, objective lens 42 can also comprise high index glass. The function of first objective lens 46 and second (or outer) objective lens 42 can be to project the image of the iris opening at the prescribed spot diameter, with a high degree of light uniformity, no objectionable artifacts inside or outside the spot, and with good edge definition across the entire range of working distances and iris openings.

As shown in FIG. 9, condensing lens 43 captures and focuses the light from LED light source 50 toward larger condensing lens 45 which in turn focuses the light through iris 60. Particular attention can be paid to the selection of glasses and lens curvatures that yield a minimal amount of lateral chromatic aberration at the edge of the spot. The luminaire can utilize a classic Koehler optical design (projector optics) with an optical efficiency of, for example, about 71%.

The compact LED luminaire optics 40 shown in FIG. 9 particularly can be optimized with respect to one or more of the following factors: (1) large LED die combined with wide beam angle; (2) high collection efficiency in a compact and lightweight luminaire system; (3) simplicity of the optics train (minimal number of optical components including an adjustable iris diaphragm and a folding mirror); (4) high spot quality (uniformity and light output) at the prescribed working distance, for example, about 16 inches and for the full range of prescribed working distances, for example, about 10 inches to about 25 inches; and (5) a projected spot that does not have a "memory" of the square shape of LED light source 50 or its surface structure.

Headlight device 10 can be configured for either battery powered or direct powered use. For example, headlight device 10 can be configured for direct power and battery power, respectively. Such a headlight device can be designed to provide illumination to aid visualization during minor surgical, diagnostic, or therapeutic procedures.

Headlight device 10 can be a self-contained headlight system that can be operated using either battery or direct power supply. Using a battery pack 76 (see FIG. 2) can give a surgeon complete portability allowing unrestricted movement in and around the operating suite. Power can for example be supplied by a medical grade 12 VDC, 3.0 A power supply. The direct power supply option 72 and 74 (see FIG. 2) can be used as a primary power source for unlimited operating time, or as a back-up to the battery system. A 15 VDC supply can power a linear power supply which can power LED light source 50 and air moving device 30.

When headlight device 10 is powered by rechargeable battery packs, controller board 14A can monitor the remaining battery power available and can provide both audible and visual feedback to the user. For example and without limitation, a five segment LCD bar display on the battery 76A can provide visual feedback to the user representing its remaining charge status (0% to 100% in 20% increments). An audible notification can also be delivered to the user when a low battery condition is detected. A three-tone cycle can sound at approximately fifteen minutes of charge remaining and can be repeated every three minutes to notify the user that a new battery pack generally designated 76 can be inserted or that a direct power supply can be attached to headlight device 10.

Regarding power supply as mentioned previously, headlight device 10 can support AC line input. In some embodiments, as explained below, AC power supply can be connected to a transformer that converts the power supply to a DC power supply with a power connector 14C of headlight device 10 being connected to the transformer. AC (wall power) operation option can include 3 distinct components: AC Power Cord 70 (see FIG. 2), Medical Grade Switching Power Supply, and a replaceable low voltage power cord (not shown). AC Power can be delivered through a detachable country specific AC power cord 70 as shown in FIG. 2 connecting to a medical grade power supply using standard IEC connector 70A and a wall plug 70B. AC power cords can include USA/JAPAN, UK, EU, AUSTRALIA, style connectors. AC Power cord length can be any desirable length, for example, about 8 feet+/−about 2 feet.

In some embodiments, connector 14C can be a DC output side of a power supply and can have a 20 inch output cable with a connector for mating to headlight device 10. In this manner, a power supply can be connected to headlight device 10 via a robust low voltage DC power cord 72. The length of power cord 72 can be any desirable length that will allow for desired movement of the user, for example, about 20 feet. Low voltage DC power cord 72 can terminate in connector end 72A and connector end 72B. Connector end 72B can be plugged into a connector on a transformer 74 or an umbilical cord (not shown) in transformer 74. The umbilical cord can also be any desirable length. Connector end 72A can be electrically connected with connector 14C extending from controller housing 14. Low voltage DC power cord 72 can be capable of withstanding heavy abuse including frequent crushing forces caused by foot traffic and being rolled over by wheeled medical devices to maintain electrical safety and conductivity. Low Voltage DC power cord 72 from the power supply to headlight device 10 can be flexible enough to facilitate easy coiling into a coil. Electrical connections from DC power cord 72 to headlight device 10 and connector 14C can be polarity non-specific. For example, controller 14A can determine polarity and compensate for either condition. DC electrical connections can be robust, securely locking into place and capable of 3000 cycles without producing electrical intermittence and reduction in insertion/retention forces to less than about 3 lbs. Controller 14A can have connector 14C connected thereto. Connector 14C can comprise have a low voltage DC cable terminating in a connector for connection to a battery and holster or DC power supply cable.

In addition to or alternatively, headlight device 10 as shown in FIG. 2 for example can include a battery system 76 that can comprise a battery 76A, a connection cable 76B and a battery holster 76C, as well as battery charger (not shown). Connection cable 76B can comprise a low voltage DC cable terminating in a connector 76B$_1$ for connection to connector 14C. Cable 76B and connector 76B$_1$ can be the same as is used on the switching power supply that switches AC current to DC current. The circuitry in battery holster 76C can provide an Audible Low Battery Warning function. The targeted volume of the tone can be loud enough to be heard in a busy operating room without being a distraction and can operate at different hertz and for different amounts of time to help indicate the level of battery power still available. Tones measured by an external microphone can approximate a sine wave. Battery 76A can have a charge state indicator 76D, such as a Liquid Crystal Display (LCD) Fuel Gauge. The battery charger (not shown) can be, for example, an INSPIRED ENERGY® single bay charger.

The color temperature for LED light source 50 can be set for the luminaire 20 based on the LED package used. Color temperature variability can be defined by standard binning by LED manufacturer. IR content can be a low percentage of total light output as measured from the luminaire. In one aspect and for example, UV content can also be a low percentage of total light output as measured from the luminaire. The light output of LED light source 50 can vary based on use and the LED package used within Luminaire 20. For example, the light output of LED light source 50 can be in one aspect no less than about 350 lumens at full power.

Iris 60 can have different numbers of leafs to provide adjustability for dilation or constriction of iris 60. Iris 60 can be, for example, a 10 to 12 leaf iris that can provide a varying illumination spot diameter. The peak illuminance of the luminaire large spot can vary depending on the user's preference and the LED package used on luminaire 20. The peak illuminance of the luminaire large spot can be bright enough to be used in surgery. The spot can advantageously have no perceptible dark center. The design of luminaire 20 can minimize objectionable artifacts outside or inside the illumination spot. Headlight spot quality and spot definition at a normal working distance (about 16 inches) can be preserved through entire excursion of light source dimmer. Headlight device 10 can include different settings for the level of intensity of the light generated by light source 50. Depending on the needs of a user, a wide range of settings for the level of light intensity can be employed. For example, in one aspect headlight device 10 can have a 4 position rotary switch (Off, Low, Med, and High) (not shown). Such a switch can be located on head wearable portion 12 and be easily accessible to the right hand of the user as well as to an attendant. Luminaire 20 and headlight device 10 can automatically switch to the low setting for the level of light intensity in the event of overheating. If overheating continues in a low setting, headlight device 10 can switch to a lower level default mode. Controller housing 14 can house a thermostatically controlled cooling fan that can be calibrated to maintain luminaire housing 24 that houses LED light source 50 at a predetermined temperature.

Figure 10:
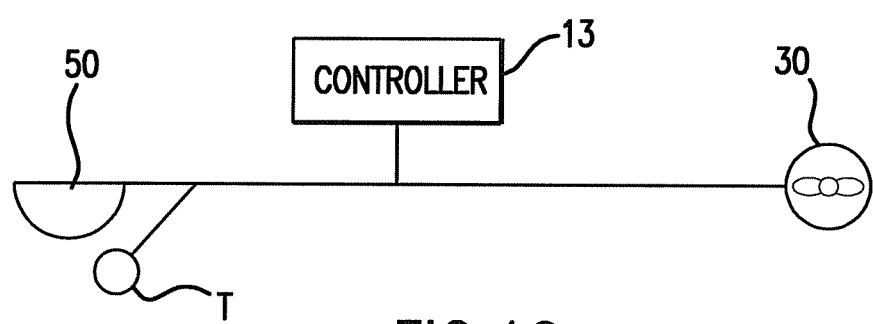
FIG. 10 illustrates a schematic diagram of an embodiment of components that can be used to control the temperature of a light source in accordance with the subject matter disclosed herein.

For example, as shown in FIG. 10, a temperature sensor T, such as a thermostat for example, can be disposed at least proximate or in contact with LED light source 50 to measure or determine the temperature of LED light source 50. Temperature sensor T can be electrically connected to, or at least in communication with, controller 13 and/or air moving device 30, such as a cooling fan. Alternatively, temperature sensor T can be electrically connected to, or at least in communication with, controller 13 and controller 13 can be electrically connected to, or at least in communication with, air moving device 30. As the temperature sensed by the temperature sensor T changes, controller 13 can automatically control temperature of LED light source 50. For example, controller 13 can automatically control the speed of air moving device 30, and thus the speed of airflow generated thereby. Further, controller 13 can automatically control an intensity of the light from LED light source 50. These measures can facilitate control of the temperature of LED light source 50, as described further below.

Headlight device 10 can in one aspect have a weight that can be less than or equal to about 400 grams with a target weight of about 330 grams. Headlight device 10 minus the padding can be cleaned with common cleaning and disinfection agents used in hospitals, e.g. 70% isopropyl alcohol and CAVICIDE® wipes. Sterilization may not be required. Headlight device 10 can be designed to hold up to normal every day handling in the operating room environment, including for example being dropped onto a tile floor from at least three feet. Gown clips can be supplied with each headlight device 10 to securely attach the electric cord to the surgical gown. All materials can be latex free.

LED headlight device 10 typical use can for example be four or more surgeries per day with about an hour per surgery average for about five days per week. For such average use, headlight device 10 can provide reliable service for at least three or more years. Headlight device 10 can comprise one luminaire and optionally head wearable portion, two battery packs, one battery holster, one battery charger with power supply, one AC power supply, one DC cable, and accessories and replacement parts.

Controller board 14A in headlight device 10 can include software to control the intensity of light generated by LED light source 50 and air moving device 30, such as a cooling fan, that draws air at a very low flow rate through vents 36A, 36B on the side and back of luminaire 20 thereby cooling LED light source 50 as necessary. The software can reside for example in controller board 14A. There can also be software located in battery pack 76 that can provide audible notification to the user when the battery charge remaining is nearing its end.

The software can be a computer readable medium and can provide certain functionalities to controller board 14A of headlight device 10. The software can allow controller board 14A to be able to read the temperature of LED light source 50 to within a small temperature range. The software can allow controller board 14A to detect an open circuited LED temperature sensor as indicated by a temperature reading of below a predetermined temperature, for example, below freezing. The software can allow controller board 14A to be able to detect an over-temperature condition or a short circuited LED temperature sensor as indicated for example by a temperature reading above a predetermined temperature. The software can allow controller board 14A, upon detection of an out of range temperature condition, for example, temperatures outside of a range between the temperature below the temperature indicating an open circuited temperature sensor and the temperature indicating an over-temperature condition to be able to put LED light source 50 into a fault condition that is below the lowest setting of the level of light intensity for headlight device 10, set the fan to its lowest speed, and/or lock the system from use until the power is cycled.

The range operating temperatures of headlight device 10 can vary depending on the LED package used and the desired need for energy efficiency and light output. During a low normal operating LED temperature range, the software can allow controller board 14A to automatically set air moving device 30 to a minimum speed. During a midrange normal operating LED temperature range, controller board 14A can automatically vary the speed of air moving device 30 ranging from a low speed to a high speed and proportional to the temperature. Thus, at this midrange temperature range, the speed of air moving device 30 can be variable. During a high normal operating LED temperature range where overheating may become a concern, the software can allow controller board 14A to automatically set air moving device 30 to a high speed, such as a maximum speed for air moving device 30. During a high temperature condition above the normal operating temperature range, the software can allow controller board 14A to automatically set air moving device 30 to operate at its maximum level of performance and the light source 50 can be reduced to its lowest setting for the level of light intensity. The software can allow controller board 14A to be able to automatically switch to the lowest setting for the level of light intensity in the event of overheating. If overheating continues in this lowest setting, controller board 14A can further reduce the level of light intensity below the lowest setting of the LED through the software.

The software can allow controller board 14A to be capable of controlling the LED intensity as selected by the four-position rotary switch. The settings of control can, for example, be: Off, Low, Medium, and High. Software in either battery pack 76 or controller board 14A or any other suitable location can provide an audible notification upon detection of a low battery condition. These audible notifications can vary in number and in timing. For example, a single audible notification can occur at a predetermined estimated time until the battery is expected to die with the audible notification occurring until the battery dies. Another example is provided below:

| | |
|---|---|
| 15 Minutes Remaining: | 1 Audible Notification Cycle |
| 12 Minutes Remaining: | 1 Audible Notification Cycle |
| 9 Minutes Remaining: | 2 Audible Notification Cycle |
| 6 Minutes Remaining: | 3 Audible Notification Cycle |
| 3 Minutes Remaining: | Audible Notification Cycle Repeats until the Battery is Fully Discharged |

For example, when a low-battery condition is detected, the following notification sequences can occur. A tone sequence can be played when there is about 15 minutes of power remaining to indicate that there are about 15 minutes (+/−about 1 minute) remaining of power. A tone sequence can then be played one time at about 12 minutes of power remaining to indicate that there are about 12 minutes (+/−about 1 minute) remaining of power. At about 9 minutes of power remaining, a tone sequence can be played for a first time with a time interval followed by the tone sequence being played a second time to indicate that there are about 9 minutes (+/−about 1 minute) remaining of power. At about 6 minutes of power remaining, a tone sequence can then be played for a first time followed by a time interval followed by the tone sequence being played a second time that is then followed by another time interval and the tone sequence being played a third time to indicate that there are about 6 minutes (+/−about 1 minute) remaining of power. With about 3 minutes of power remaining, tone sequences can be repeated with time intervals in between the tones to indicate that the battery is about to die until the power is off and/or the battery dies or is recharged or replaced.

Headlight device 10 as described herein can utilize an LED light source with an active cooling system. A thermostatically-controlled cooling fan can draw air at a very low flow rate through vents on the side and back of the luminaire, quietly cooling the LED. The air can be drawn through a system of vents and tubes, or ducts, and can be gently exhausted behind the surgeon. The headlight device can be designed to provide illumination to aid visualization during minor surgical, diagnostic, or therapeutic procedures. For example, as mentioned above, the headlight device can be used in neonate trans-illumination, ophthalmic procedures, or with photosensitive patients who have received photosensitizing agents (hematoporphyrin derivatives) within three months prior to the operation.

Embodiments of the present disclosure shown in the drawings and described above are exemplary of numerous embodiments that can be made within the scope of the appending claims. It is contemplated that the devices and related methods can comprise numerous configurations other than those specifically disclosed.

What is claimed is:
1. A headlight device comprising:
   a luminaire comprising:
      a luminaire housing comprising a first end, a second end opposing the first end, and a heat sinking chamber disposed therebetween, wherein a plurality of luminaire vents are disposed in a ring about the heat sinking chamber of the luminaire housing;
      an optical assembly disposed in the first end of the luminaire housing;

a heat sink and a light source disposed in the heat sinking chamber of the luminaire housing; and a venting tube extending from the second end of luminaire housing;

an air moving device provided outside of the luminaire housing, wherein the air moving device is configured to generate an airflow by pulling air into the luminaire via the plurality of luminaire vents, moving the pulled air across the heat sink thereby heating the air, expressing the heated air outside of the luminaire housing via the venting tube, and expelling the heated air from the air moving device outside of the luminaire housing; and an exhaust tube connecting the venting tube of the luminaire and the air moving device, wherein the exhaust tube is configured to flow the heated air along a path from the venting tube to the air moving device.

2. The headlight device according to claim 1, further comprising a controller in communication with the luminaire and the air-moving device.

3. The headlight device according to claim 2, wherein the controller comprises a controller housing in which a controller board and the air moving device reside.

4. The headlight device according to claim 3, wherein the controller housing further comprises an air flow tube connected to the exhaust tube and configured to direct air flow from the exhaust tube to the air moving device.

5. The headlight device according to claim 2, wherein the controller is operable to automatically control temperature of the light source.

6. The headlight device according to claim 5, wherein the controller is operable to automatically control a speed of the air moving device and an intensity of the light generated from the light source to control the temperature of the light source.

7. The headlight device according to claim 6, wherein the controller is operable to set the air moving device to a low speed for a predetermined temperature range.

8. The headlight device according to claim 6, wherein the controller is operable to set the air moving device at a variable speed ranging from a low speed to a high speed and proportional to the temperature for a predetermined temperature range.

9. The headlight device according to claim 6, wherein the controller is operable to set the air moving device to a high speed for a predetermined temperature range.

10. The headlight device according to claim 6, wherein the controller is operable to set the air moving device to a high speed and the light source to a lowest setting of a level of the intensity of light for a predetermined temperature range.

11. The headlight device according to claim 5, wherein the controller is operable to switch intensity of the light source among the settings of Off, Low, Medium, and High.

12. The headlight device according to claim 1, wherein the light source comprises at least one light emitting diode (LED).

13. The headlight device of claim 12, wherein the luminaire further comprises:

a circuit board with an opening therethrough, the LED being electrically connected to the circuit board;

a first heat sink comprising a thermally conductive board having a protrusion extending through the opening to be in thermal contact with the LED; and a second heat sink thermally coupled to the thermally conductive board.

14. The headlight device of claim 1, wherein the optical assembly comprises:

a condensing lens;
an objective lens;

an iris control placed between the condensing lens and objective lens; and a folding mirror disposed between the condensing lens and objective lens.

15. The headlight device of claim 14, wherein the condensing lens is disposed in close proximity to the LED and is shaped as a meniscus lens.

16. The headlight device of claim 1, wherein the optical assembly comprises:

a first condensing lens and a second condensing lens;
a first objective lens and a second objective lens;
an iris control disposed between the condensing lenses and objective lenses; and
a folding mirror disposed between the first objective lens and the second objective lens.

17. The headlight device according to claim 1, wherein the air moving device comprises a fan.

18. The headlight device according to claim 1, wherein the exhaust tube comprises a head wearable portion to which the luminaire is attached.

19. The headlight device according to claim 1, further comprising a head wearable portion to which the luminaire and the exhaust tube is attached.

20. The headlight device according to claim 19, wherein the air moving device is at the rear of the head wearable portion and the exhaust tube extends around a side of the head wearable portion.

21. The headlight device according to claim 1, further comprising a battery pack, the battery pack being operable to alert the user when the battery is running low on power.

22. A method of operating a headlight device, the method comprising:

providing a headlight device comprising:
a luminaire comprising:
a luminaire housing comprising a first end, a second end opposing the first end, and a heat sinking chamber disposed therebetween, wherein a plurality of luminaire vents are disposed in a ring about the heat sinking chamber of the luminaire housing;
an optical assembly disposed in the first end of the luminaire housing;
a heat sink and a light source disposed in the heat sinking chamber of the luminaire housing;
a venting tube extending from the second end of the luminaire housing;
an air moving device provided outside of the luminaire housing; and
an exhaust tube connecting the venting tube and the air moving device; and
generating an airflow by the pulling air into the plurality of luminaire vents via the air moving device;
controlling a temperature of the light source by flowing the air through the luminaire vent and over the heat sink thereby heating the air;
expressing heated air from the luminaire housing via the venting tube;
flowing heated air from the venting tube into the exhaust tube and through the exhaust tube to the air moving device; and
expelling the heated air out through the air moving device, which is disposed outside of the luminaire.

23. The method according to claim 22, wherein controlling the temperature of the light source further comprises setting the air moving device to a low speed.

24. The method according to claim 22, wherein controlling the temperature of the light source further comprises setting the air moving device at a variable speed ranging from a low speed to a high speed and proportional to the temperature.

25. The method according to claim 22, wherein controlling the temperature of the light source further comprises setting the air moving device to a high speed.

26. The method according to claim 22, wherein controlling the temperature of the light source further comprises setting the air moving device to a high speed and the light source to a lowest setting of a level of an intensity of the light generated by the light source.

27. The method according to claim 22, wherein controlling the temperature of the light source further comprises switching the intensity of the light source among the settings of Off, Low, Medium, or High.

28. The method according to claim 22, wherein the headlight device further comprises a battery pack and the battery pack is operable to provide an alert when the battery is running low on power.

29. A headlight device comprising:
a luminaire disposed proximate a front portion of the headlight device, the luminaire comprising:
a luminaire housing comprising a first end, a second end opposing the first end, and a heat sinking chamber disposed therebetween, wherein a plurality of luminaire vents are disposed in a ring about the heat sinking chamber of the luminaire housing;
an optical assembly disposed in the first end of the luminaire housing;
a heat sink and a light source disposed in the heat sinking chamber of the luminaire housing; and
a venting tube extending from the second end of luminaire housing;
an air moving device disposed proximate a rear portion of the headlight device which at least partially opposes the front portion, the air moving device also being disposed outside of the luminaire housing and configured to generate an airflow by pulling air into the luminaire via the plurality of luminaire vents, moving the pulled air across the heat sink thereby heating the air, and expelling the heated air from the rear portion of the device; and
an exhaust tube connecting the venting tube extending from the luminaire to the air moving device to facilitate air flow of the heated air from the heat sink in the front portion of the device to the rear portion of the device to expel the heated air.

30. The method according to claim 22, wherein providing the headlight device comprises providing a front portion comprising the luminaire and providing a rear portion at least partially opposing the front portion, wherein the rear portion comprises the air moving device, and wherein the exhaust tube connects the luminaire and the air moving device for flowing the air from the front portion of the device to the rear portion of the device.

31. The headlight device of claim 1 wherein the light source is thermally coupled to the heat sink.

32. The headlight device of claim 1 wherein the light source is thermally coupled to more than one heat sink.

* * * * *